United States Patent
Srebotnik et al.

(10) Patent No.: US 9,206,292 B2
(45) Date of Patent: Dec. 8, 2015

(54) METHOD FOR PRODUCING LIGNIN DERIVATIVES

(75) Inventors: Ewald Srebotnik, Vienna (AT); Thomas Ters, Vienna (AT); Karin Fackler, Vienna (AT); Kurt Messner, Vienna (AT); Ortwin Ertl, Graz (AT)

(73) Assignee: ANNIKKI GMBH, Graz (AT)

( * ) Notice: Subject to any disclaimer, the term of this patent is extended or adjusted under 35 U.S.C. 154(b) by 0 days.

(21) Appl. No.: 14/006,849

(22) PCT Filed: Mar. 2, 2012

(86) PCT No.: PCT/EP2012/053592
§ 371 (c)(1),
(2), (4) Date: Oct. 9, 2013

(87) PCT Pub. No.: WO2012/126709
PCT Pub. Date: Sep. 27, 2012

(65) Prior Publication Data
US 2014/0038246 A1 Feb. 6, 2014

(30) Foreign Application Priority Data
Mar. 24, 2011 (EP) .................................. 11002445

(51) Int. Cl.
*C08H 7/00* (2011.01)
*C08H 8/00* (2010.01)
*D21C 3/20* (2006.01)
*D21C 11/00* (2006.01)
*C12P 1/00* (2006.01)

(52) U.S. Cl.
CPC .. *C08H 6/00* (2013.01); *C08H 8/00* (2013.01); *C12P 1/00* (2013.01); *D21C 3/20* (2013.01); *D21C 11/0007* (2013.01)

(58) Field of Classification Search
None
See application file for complete search history.

(56) References Cited

U.S. PATENT DOCUMENTS 5,374,555 A 12/1994 Pokora et al.

FOREIGN PATENT DOCUMENTS

| DE | 37992 | 1/1887 |
|---|---|---|
| DE | 197 00 902 A1 | 7/1998 |
| DE | 197 00 904 A1 | 7/1998 |
| DE | 197 00 906 A1 | 7/1998 |
| DE | 197 00 907 A1 | 7/1998 |
| DE | 197 01 015 A1 | 7/1998 |
| DE | 197 00 908 A1 | 8/1998 |
| WO | WO 98/31729 A1 | 7/1998 |
| WO | WO 98/31762 A1 | 7/1998 |
| WO | WO 98/31763 A1 | 7/1998 |
| WO | WO 98/31764 A1 | 7/1998 |

OTHER PUBLICATIONS

Ibarra et al. Enzyme and Microbial Technology 35 (2004) 173-181.*
Abstract of Keller, B. et al. "Specific localization of a plant cell wall glycine-rich protein in protoxylem cells of the vascular system," Proc. Natl. Acad. Sci USA, vol. 86, No. 5, 1989, pp. 1529-1533.
Abstract of Liang, H. et al. "Improved Sugar Release from Lignocellulosic Material by Introducing a Tyrosine-rich Cell Wall Peptide Gene in Poplar," Clean, vol. 36, Issue 8, 2008, pp. 662-668.
Abstract of Whitmore, F.W, "6 Lignin-protein complex in cell walls of Pinus elliottii: Amino acid constituents," Phytochemistry, vol. 21, Issue 2, 1982, pp. 315-316.
Berlin, A. et al. "Inhibition of cellulase, xylanase and beta-glucosidase activities by softwood lignin preparations," Journal of Biotechnology, vol. 125, 2006, pp. 198-209.
Ibarra, D. et al. "Isolation of high-purity residual lignins from eucalypt paper pulps by cellulase and proteinase treatments followed by solvent extraction," Enzyme and Microbial Technology, vol. 35, 2004, pp. 173-181.
Iiyama, K. et al. "Cell Wall Biosynthesis and Its Regulation," Forage Cell Wall Structure and Digestibility, Eds. H.G. Jung et al., ASA-CSSA-SSSA, Madison, WI, USA, 1993.
International Search Report issued in PCT/EP2012/053592 mailed Jun. 1, 2012.
Keller, B. "Structural Cell Wall Proteins," Plant Physiology, vol. 101, 1993, pp. 1127-1130.
Written Opinion of the International Searching Authority issued in PCT/EP2012/053592 mailed Jun. 1, 2012.

* cited by examiner

*Primary Examiner* — Nashaat Nashed
(74) *Attorney, Agent, or Firm* — Birch, Stewart, Kolasch & Birch, LLP

(57) ABSTRACT

A method for producing lignin derivatives from technical lignins by treatment with proteolytic enzymes (proteases), characterized in that the proteolytic treatment of the technical lignins significantly reduces the molar mass thereof.

8 Claims, 2 Drawing Sheets

METHOD FOR PRODUCING LIGNIN DERIVATIVES

The substantial structure-forming elements of the lignocellulose are cellulose, hemicellulose and lignin. Although proteins are also integral parts of lignocellulose and are deposited in the cell wall in the course of the biosynthesis, their biological function in the cell wall, however, is still largely unknown or simply a matter of speculation [1, 5].

It is formally possible, and in individual cases it has also been known, that during the process of lignification of plant cell walls, there are developed covalent bonds between lignin and proteins [1-5]. There is made the assumption that such cross-lining, e.g. by way of radial coupling between tyrosine residues in proteins and phenolic groups, may occur in the lignin; and there are indications that protein deposition and lignification are definitely closely related to each other [4, 5]. Thus proteins as such may not only be present in the plant cell wall but rather also be cross-linked with other cell wall components. There are still outstanding specific structural analyses, which could find prove therefore. There are further also not available any reports on the isolation and characterization of possible lignin-protein conjugates from cellulose, which would prove that lignin really is composed of a considerable percentage of such conjugates.

U.S. Pat. No. 5,374,555 [5] discloses a method for the delignification of lignocellulose with proteases. In several examples there is shown that treating lignocelluloses with protease will simplify and promote the extraction of lignin from the lignocellulose. This effect has been put down to proteins forming a cross-linked matrix in lignocellulose, which is, e.g. bound to lignin, which is why the hydrolysis of this protein network simplifies the removal of lignin from the lignocellulose. In the U.S. Pat. No. 5,374,555 [5] there is, however, neither disclosed that the extracted lignin itself could contain significant amounts of protein or that this protein has a substantial portion of the molar mass of this hypothetical lignin-protein conjugate; nor a possible preparation of peptides and/or amino acids from the hydrolysate.

Liang et al. [3] describe a molecular biological method for the in-situ introduction of peptide-lignin cross-linking in the plant cell wall in order to promote the release of polysaccharides by a subsequent treatment of the lignocellulose with proteases. A possible influence of the protease treatment on the physico-chemical characteristics, for example, on the molar mass of the treated peptide-lignin conjugates, however, is not mentioned at all.

The present invention now is based on the finding that lignin-protein conjugates do not simply exist in lignocellulose but, surprisingly, rather constitute a substantial amount of the entire lignin. Namely, tests performed by the inventors have shown that the treatment with protease enzymes is suitable to significantly reduce the molar mass of technical lignin in order to thereby obtain a lignin derivative having improved material characteristics. In one of the embodiments of the invention thus technical lignin is treated with a protease enzyme or a mixture of different protease enzymes in an amount and under reaction conditions, which is/are suitable to cleave the protein(s) bound to the technical lignin and, in this way, significantly reduce the molar mass of the technical lignin and obtain a de-proteinized lignin derivative. The comparably low molar mass of the cleaved peptides and/or amino acids as well as the particular chemical characteristics provide in a further embodiment of the invention the cleavage thereof from the remaining lignin derivative by means of additional procedural steps such as, e.g., ultra and nano filtration, extraction, precipitation or chromatography. In another embodiment of the invention thus the peptides and amino acids present following the treatment with protease enzyme(s) in the hydrolysate are separated from the lignin derivative and further processed into special products.

One advantage of the inventive method with regard to conventional methods for the reduction of the molar mass of technical lignin such as, e.g., thermal cleavage and cleavage via metal catalysts, is the processing under mild conditions, namely at mild temperatures. In this way, the lignin cannot disintegrate and may substantially remain in its natural condition regarding its chemical structure. What are the technical advantages of small lignins?

An especially substantial advantage of the inventive method is the provision of lignin derivatives, which may be converted to polymerisates with higher molar mass, and thus activated, in a much better way by means of enzymes, for example laccase, than de-proteinized lignin. As explained in the following, such polymerisates have shown to be excellent binding agents for wooden composites.

DE 37992 C2 describes a method for the preparation of a binding agent, wherein technical lignin is converted to an active binding agent for wooden composites by way of polymerization with laccase and atmospheric oxygen. In DE 19700908 A1 (WO 98/31729) there is prepared in a similar way an activated intermediate product from industrial lignin, which is then reacted in the presence of atmospheric oxygen and phenoloxidizing enzymes, for example, laccase, with not activated technical lignin, thus forming polymeric lignin products having a substantially higher molar mass than in the control reaction carried out without activated lignin. The higher molar mass of such activated technical lignins has proven to be the equivalent of an increased cohesive force when used as a binding agent. A rather comprehensive oxidation of the lignin has proven advantageous. In DE 19700908 A1 (WO 98/31729), for example, it was possible to achieve an increase of the tensile strength of chip boards from 6 MPa to 11 MPa, corresponding to an increase of molar mass of 16.6% if activated kraft lignin with a molar mass of 6,300 g/mol was used instead of non-activated kraft lignin with a molar mass of 5,400.

Now there has surprisingly been found that the de-proteinized lignin derivative obtained by the inventive method by proteolytic treatment has a substantially increased reactivity and thus activatability than not de-proteinized technical lignin. The activation of a technical lignin with laccase and atmospheric oxygen, which was carried out in a similar way as described in DE 37992 C2 as well as DE 19700908 A1 (WO 98/31729), resulted in an increase of the molar mass by 40%, whereas with the inventive de-proteinized lignin derivative of the same technical lignin under otherwise identical reaction conditions it was possible to obtain a faster polymerization and an increase of the molar mass by 167%. Obviously the de-proteinization of a technical lignin to a high extent increases the reactivity thereof for an enzymatically catalyzed and oxidized polymerization. This finding forms the basis of the technical benefit of the present invention, because according to DE 37992 C2 as well as DE 19700908 A1 (WO 98/31729) it is just that polymerizability and the activation of lignin associated therewith that is decisive with regard to the technical suitability of lignin derivatives as a binding agent. According to DE 19700902 A1, DE 19700904 A1, DE 19700906 A1, DE 19700907 A1 and DE 19701015 A1 the polymerizability and the activation of lignin associated therewith furthermore is of great importance for the technical suitability of lignin derivatives as coating agents for papers and other plant fibres, as highly reactive reagents for the preparation of duroplasts, for the preparation of fibrereinforced compound materials as well as an binding agent for wooden composites. Also for these applications there is to be expected a technical benefit associated with the activatability of technical lignin obtainable by means of the method according to the invention.

WO 98/31762, WO 98/31763 and WO 98/31764 also describe the use of technical lignins or soluble technical lignin/carbohydrate fractions from lignocellulosic substrates of phenoloxidizing enzymes for the polymerization.

According to the state of the art, there is to be made the assumption that the reduction of the molar mass of a technical lignin by protease treatment will cause a release of peptides and/or amino acids in corresponding amounts. Since the percentage of the lignin fractions according to the invention may be rather high, it follows that by using the inventive method it is possible to prepare products from technical lignins, which advantageously are substantially composed of peptides and/or amino acids and which are contaminated only to a rather small extent by lignin, which makes it seemingly economical reasonable to prepare peptides and/or amino acids from raw products produced according to the inventive method.

The following examples are intended for the illustration of the present invention. In the examples 1 to 3, lignin is prepared from straw, and it is characterized in terms of molar mass and lignin content. Example 4 illustrates on the basis thereon the proper core of the invention, namely the significant reduction of the molar mass of lignin by means of treatment with protease.

EXAMPLE 1

Preparation of a Technical Lignin on a Laboratory Scale

Wheat straw is crashed to a particle size of about 2 cm. 2.5 g of crashed wheat straw is suspended in a 500 ml reaction vessel in 200 ml of a solution consisting of water and ethanol (50:50). The suspension is heated to 50° C. in a water bath, thermally regulated, and the pH of the suspension is adjusted to a starting pH of 13 by aqueous NaOH solution. The mixture is then continuously stirred at 200 rpm, 70° C., and 24 h.

Subsequently, the solid is filtered off, and the clear filtrate is adjusted to a pH of 2.0 by phosphoric acid. The precipitate formed was dissolved in dimethylformamide (DMF) and partitioned into high- and low-molecular fractions using preparative gel chromatography on Sephadex LH60 in DMF. The DMF in the individual fractions was evaporated from the fractions in high vacuum, and the solid residues were homogenized in the mortar.

EXAMPLE 2

Assessment of the Molar Mass

A suitable sample amount of a higher-molecular fraction of example 1 was dissolved in 10 mM NaOH and then subjected to molar mass assessment by way of HPSEC in an Agilent 1200 HPLC system. The HPSEC System consisted of three serially connected columns by Tosoh Bioscience (G3000PW, G4000PW and G4000PW), with 10 mM NaOH as a solvent. Calibration was performed with polystyrol sulfonate (PSS). The assessment of the molar mass distribution of the sample was carried out by evaluation of the UV chromatograms recorded at the absorption maximum of lignin (280 nm).

EXAMPLE 3

Assessment of the Extinction Coefficient

Exactly weighed-in amounts of lignin fractions of example 1 were, on the one hand, analysed with regard to the protein content (CHN analysis) and, on the other hand, dissolved in DMF, followed by the assessment of the UV absorption of these solutions at 280 nm in the spectrometer. The extinction coefficient is calculated by division of the weighed-in amount by the total absorption at 280 nm.

Figure 1:
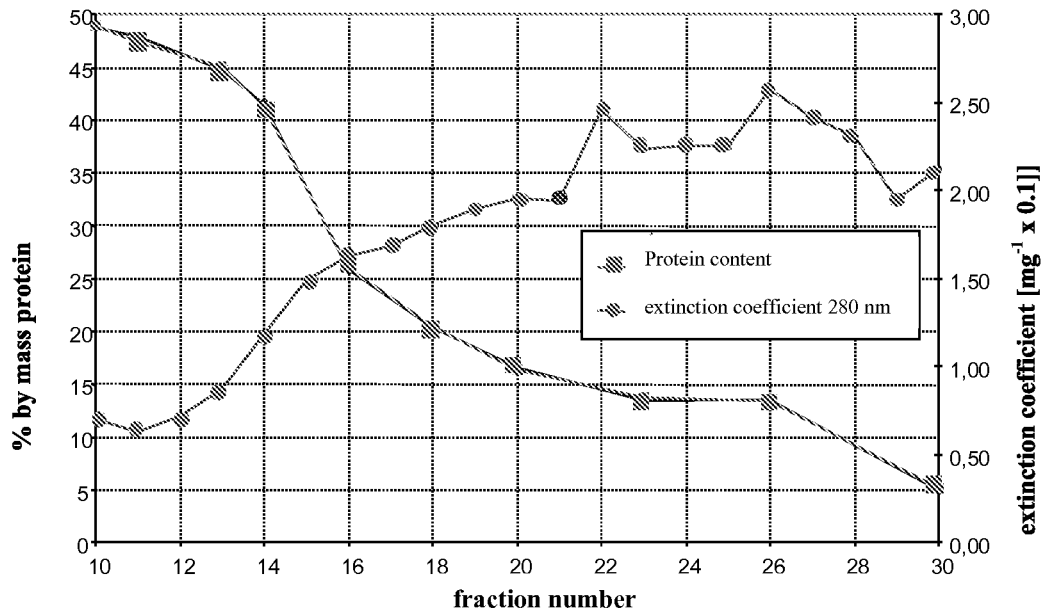
FIG. 1 is a graph showing the extinction coefficient at 280 nm and protein content of the fractions from the preparative gel chromatography of example 1.

In FIG. 1 the extinction coefficient at 280 nm and protein content of the fractions from the preparative gel chromatography of example 1 is shown. The molar mass of the fractions is increasing with increasing fraction number.

A typical result is depicted in the figure. Accordingly, the extinction coefficient of the lignin is increased at the absorption maximum of 280 mu that is typical for lignin from high (fraction number 10) to low (fraction number 30) molar masses by a factor 4-5 from about 5 $mg^{-1}$ to 20-25 $mg^{-1}$. Under the assumption according to the state of the art that the extinction coefficient of pure lignin is relatively constant and that the fractions examined in the present invention with the highest extinction coefficients (fractions 21-30) are composed of nearly pure lignin, then the high-molecular fractions have to be composed of up to 80% (fraction 9) non-lignin. Without wishing to be bound by any theory, the inventors, in consideration of the result of example 4, assume that the above mentioned non-lignin is primarily composed of protein. The result of the protein content, which is calculated on the basis of the nitrogen content and which is also displayed in the figure, confirms this assumption: the protein content in the fractions is also decreasing with decreasing molar mass, this is increasing fraction number.

EXAMPLE 4

Treatment with Protease 5 mg of acid-precipitated technical lignin or of higher-molecular fractions of the acid-precipitated lignin according to example 1 were dissolved in 1 ml 25 mM Tris-buffer at pH 8.5, and 0.1 mg of protease from *Streptomyces griseus* (Sigma P5147) were added and stirred at 37° C. for 1 to 24 h. Alternatively, there was used protease from *Bacillus licheniformis* (Sigma P5380), trypsin or 0.1 g of a mixture of the above mentioned proteases with similar results. The reaction solution was then adjusted to a pH of 12.0 with NaOH and subjected to HPSEC analysis according to example 2.

Figure 2:
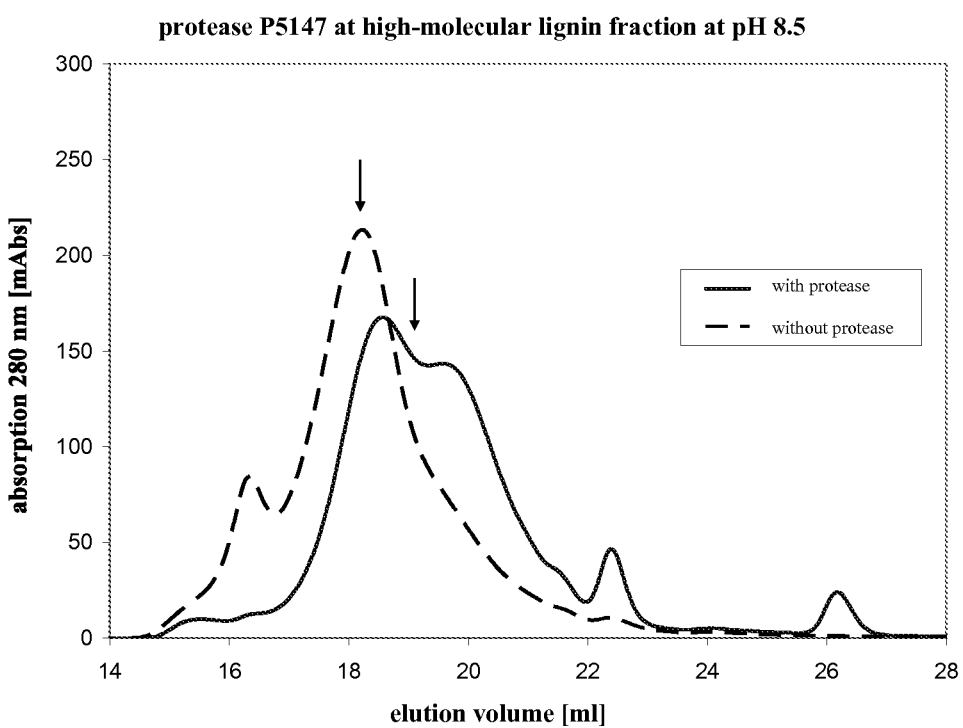
FIG. 2 is a graph showing the treatment of technical lignin prepared on a laboratory scale with protease which resulted in a significant reduction of the molar mass of originally 16,000 Da to about 6,000 Da (in the figure indicated by arrows).

A typical result is depicted in the FIG. 2. Accordingly, the treatment of technical lignin prepared on a laboratory scale with protease resulted in a significant reduction of the molar mass of originally 16,000 Da to about 6,000 Da (in the figure indicated by arrows). As easily visible by comparison of the peak areas, the molar mass distribution of the technical lignin has shifted significantly to the right, this is towards the lower molar masses, due to the treatment with protease. In particular in the high-molecular field, for example at an elution volume of about 17 ml, the difference in regard to absorption at 280 nm is a multiple thereof, thus indicating a high protein proportion.

Furthermore, this result shows that the protein cannot be a type of contamination being merely integrated into the lignin preparation by chance, as otherwise there would not have been observable a shift of the molar mass of this technical lignin due to the treatment with protease. The UV spectrum of the clearly protein-containing high-molecular fractions, moreover was typically from lignin. Hence, there are not simply involved some UV absorbing protein structures, which have been detected herein. The result rather shows that protein was bound, possibly covalently, to the lignin by a substantial interaction and that it could be successfully cleaved by way of the treatment with protease.

Similar results were also obtained with other lignin fractions and other proteases. In general, however, there was observed more influence of proteases on the molar mass of the lignin the higher the molar mass of the lignin starting material was before the treatment with protease. This is in accordance with the result of example 3, wherein the extinction coefficient of the lignin significantly was reduced at 280 nm with increasing molar mass.

EXAMPLE 5

Polymerization with Laccase 20 mg of a higher-molecular fraction of the technical lignin according to example 1 were added to 500 μl protease (5 mg/ml in water) in a concentration of 4 mg/ml at pH 8.7 according to example 4. To the control reaction was added 500 μl water instead of protease. The reaction mixtures were incubated over night at 37° C. Following adjustment to a pH of 6.0, there were added 100 μl laccase (1 U/ml in water) to each 0.9 ml of the reaction solutions and incubated at 30° C. In certain time intervals, see figures, samples were taken, diluted with 10 mM undiluted NaOH (1:10) and then subjected to a molar mass assessment by means of HPSEC according to example 2.

Figure 3:
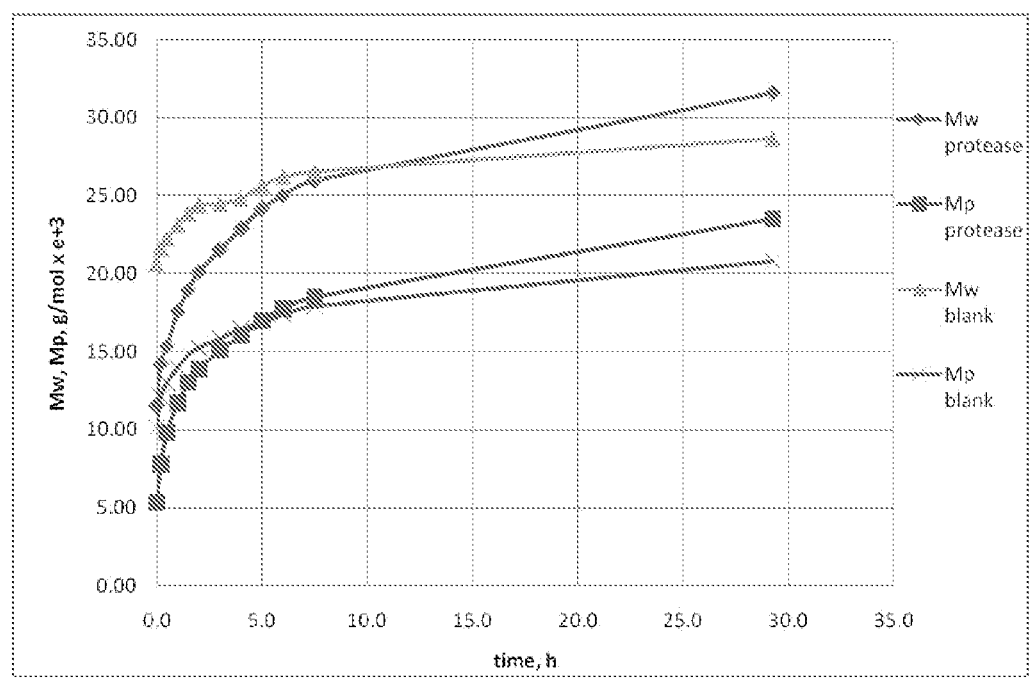
FIG. 3 is a graph showing the temporal change of the molar mass (Mp, peak maximum) as well as molar mass distribution (Mw, weight average of the molar mass) of a protease-treated („protease") as well as an untreated („blank") higher-molecular fraction of a technical lignin according to example 1 due to laccase influence.

In FIG. 3 the temporal change of the molar mass (Mp, peak maximum) as well as molar mass distribution (Mw, weight average of the molar mass) of a protease-treated ("protease") as well as an untreated ("blank") higher-molecular fraction of a technical lignin according to example 1 due to laccase influence are shown.

TABLE

Summary of the kinetic data of the polymerization of a de-proteinized as well as untreated lignin fraction by means of laccase.

| time, h | $M_n$, g/mol $10^3$ | $\Delta Mn/\Delta t$ | $M_w$, g/mol $10^3$ | $\Delta Mw/\Delta t$ | D | $M_p$, g/mol $10^3$ | $\Delta Mp/\Delta t$ |
|---|---|---|---|---|---|---|---|
| Protease-treated fraction, polymerization with 0.1 u\ml laccase | | | | | | | |
| 0.0 | 2.12 | | 11.57 | | 5.46 | 5.33 | |
| 0.2 | 2.36 | 1.20 | 14.23 | 13.30 | 6.03 | 7.79 | 12.32 |
| 0.5 | 2.53 | 0.58 | 15.38 | 3.83 | 6.08 | 9.82 | 6.78 |
| 1.0 | 2.70 | 0.33 | 17.57 | 4.38 | 6.52 | 11.70 | 3.75 |
| 1.5 | 2.89 | 0.39 | 18.96 | 2.78 | 6.57 | 13.03 | 2.66 |
| 2.0 | 3.00 | 0.22 | 20.09 | 2.26 | 6.70 | 13.89 | 1.72 |
| 3.0 | 3.14 | 0.14 | 21.55 | 1.46 | 6.87 | 15.09 | 1.20 |
| 4.0 | 3.27 | 0.13 | 22.90 | 1.31 | 7.01 | 16.06 | 0.94 |
| 5.0 | 3.42 | 0.16 | 24.18 | 1.32 | 7.06 | 17.01 | 0.98 |
| 6.0 | 3.52 | 0.10 | 25.01 | 0.83 | 7.10 | 17.75 | 0.74 |
| 7.5 | 3.67 | 0.10 | 25.98 | 0.65 | 7.08 | 18.51 | 0.51 |
| 29.3 | 4.25 | 0.03 | 31.59 | 0.26 | 7.43 | 23.52 | 0.23 |
| Untreated fraction, polymerization with 0.1 u\ml laccase | | | | | | | |
| 0.0 | 2.97 | | 20.65 | | 6.95 | 10.19 | |
| 0.2 | 3.37 | 1.97 | 21.64 | 4.95 | 6.43 | 12.13 | 9.70 |
| 0.5 | 3.58 | 0.72 | 22.29 | 2.17 | 6.23 | 13.02 | 2.97 |
| 1.0 | 3.72 | 0.28 | 23.11 | 1.64 | 6.21 | 13.99 | 1.94 |
| 1.5 | 3.88 | 0.32 | 23.87 | 1.52 | 6.15 | 14.80 | 1.62 |
| 2.0 | 3.99 | 0.21 | 24.38 | 1.02 | 6.12 | 15.25 | 0.90 |
| 3.0 | 4.07 | 0.08 | 24.48 | 0.10 | 6.03 | 15.83 | 0.58 |
| 4.0 | 4.18 | 0.11 | 24.81 | 0.33 | 5.94 | 16.46 | 0.63 |
| 5.0 | 4.23 | 0.06 | 25.64 | 0.83 | 6.06 | 16.84 | 0.38 |
| 6.0 | 4.39 | 0.15 | 26.19 | 0.55 | 5.97 | 17.39 | 0.55 |
| 7.5 | 4.52 | 0.09 | 26.55 | 0.24 | 5.88 | 17.91 | 0.35 |
| 29.3 | 5.247 | 0.03 | 28.67 | 0.10 | 5.465 | 20.81 | 0.13 |

The data given in the figure and in the table show that the polymerization of protease-treated, this is, de-proteinized, technical lignin is carried out at a much higher rate and results in a polymerisate of substantially higher molar mass than in the comparative reaction with untreated lignin. The activation of lignin by atmospheric oxygen and laccase resulted herein without protease treatment in an increase of the molar mass by 40%, whereas there could be obtained with the protease-treated lignin derivative of the same technical lignin under otherwise identical reaction conditions a higher-rate polymerization and an increase of the molar mass by 167%. Without wishing to be bound by any theory, the inventors assume that the removal of protein will result in new reaction centres at the lignin and/or will release reaction centres in the lignin masked by protein, which in the case of the effect of oxidizing agents such as, e.g., atmospheric oxygen and laccase, on the one side, causes a substantial increase of the polymerization rate and, on the other side, results in a polymerisate of substantially higher molar mass and stronger activation associated therewith.

[1] K. IIYAMA et al. (1993) Cell Wall Biosynthesis and Its Regulation. In: H. G. Jung et al. (eds.) Forage Cell Wall Structure and Digestibility, ASA-CSSA-SSSA, Madison, Wis., USA.
[2] F. W. WHITMORE (1982) Phytochemistry 21, 315-316.
[3] H LIANG et al. (2008) Clean 36, 662-668.
[4] B. KELLER et al. (1989) Proc. Natl. Acad. Sci USA 86, 1529-1533.
[5] B. KELLER (1993) Plant. Physiol. 101, 1127-1130.
[6] A. R. POKORA & M. A. JOHNSON (1994) U.S. Pat. No. 5,374,555.

The invention claimed is:
1. A method for the preparation of polymerisates of lignin derivatives which comprises the steps of:
   combining technical lignin obtained from pulping lignocellulose or a fraction thereof with a protease or with a mixture of different proteases, said protease or mixture of different proteases, being used in a suitable amount and under reaction conditions, suitable for cleaving the protein(s) bound to the technical lignin in order to reduce the molar mass of the technical lignin or of the fractions thereof, whereby a de-proteinized lignin derivative is obtained, and polymerizing said de-proteinized lignin derivative.

2. The method according to claim 1, wherein the technical lignin is obtained from wood fibres, wood shavings and/or wood chips.

3. The method according to claim 1, wherein the technical lignin obtained from lignocellulosic material is a lignosulfonate, kraft lignin, alkaline lignin and/or organosolv lignin.

4. The method according to any one of claims 1, 2, or 3, wherein peptides and/or amino acids developing upon the treatment with said protease or mixture of proteases are separated from the lignin.

5. The method according to any one of claims 1, 2, or 3, wherein the protease is at least one member selected from the group consisting of protease from *Streptomyces griseus* (Pronase, EC 3.4.24.31), protease from *Bacillus licheniformis* (EC 3.4.21.62), protease from *Staphylococcus aureus* (EC 3.4.21.19) trypsin, pepsin, bromelain and papain.

6. The method according to claim 1, wherein the lignocellulosic material is at least one member selected from the group consisting of straw, bagasse, energy crops and glumes.

7. The method according to claim 6, wherein the energy crops are at least one member selected from the group consisting of elephant grass, switch grass, and lemnas.

8. The method according to claim 4, wherein the peptides and/or amino acids developing upon the treatment with protease are separated from the lignin by means of membrane filtration and/or precipitation and/or chromatography.

* * * * *